(12) United States Patent
Stetter et al.

(10) Patent No.: US 10,241,073 B2
(45) Date of Patent: Mar. 26, 2019

(54) WIRELESS NEAR-FIELD GAS SENSOR SYSTEM AND METHODS OF MANUFACTURING THE SAME

(71) Applicant: Spec Sensors LLC, Newark, CA (US)

(72) Inventors: Joseph R. Stetter, Hayward, CA (US); David Peaslee, Newark, CA (US)

(73) Assignee: SPEC Sensors LLC, Newark, CA (US)

( * ) Notice: Subject to any disclaimer, the term of this patent is extended or adjusted under 35 U.S.C. 154(b) by 32 days.

(21) Appl. No.: 15/165,506

(22) Filed: May 26, 2016

(65) Prior Publication Data

US 2016/0349205 A1 Dec. 1, 2016

Related U.S. Application Data

(60) Provisional application No. 62/166,468, filed on May 26, 2015.

(51) Int. Cl.
*G01N 27/406* (2006.01)
*H04B 5/00* (2006.01)

(52) U.S. Cl.
CPC ....... *G01N 27/4065* (2013.01); *H04B 5/0043* (2013.01); *H04B 5/0062* (2013.01)

(58) Field of Classification Search
CPC .............. G01N 27/4065; H04B 5/0043; H04B 5/0062; H04Q 9/00; H04Q 2209/886; H04Q 2209/47
See application file for complete search history.

(56) References Cited

U.S. PATENT DOCUMENTS

| | | | |
|---|---|---|---|
| 4,924,860 | A | 5/1990 | Larsen et al. |
| 4,945,918 | A | 8/1990 | Abernathy |
| 5,064,516 | A | 11/1991 | Rupich |
| 5,173,166 | A | 12/1992 | Tomantschger et al. |
| 5,233,996 | A | 8/1993 | Coleman et al. |
| 5,239,492 | A | 8/1993 | Hartwig |
| 5,288,389 | A | 2/1994 | Yamada et al. |
| 5,429,105 | A | 7/1995 | Bennett et al. |

(Continued)

FOREIGN PATENT DOCUMENTS

| | | |
|---|---|---|
| CA | 2270809 | 10/1999 |
| DE | 2936142 | 3/1981 |

(Continued)

OTHER PUBLICATIONS

H.D. Goldberg, et al. "Screen Printing: a technology for the batch fabrication of integrated chemical-sensor array" Sensors and Actuators B: Chemical, vol. 21, p. 171-183 (Year: 1994).*

(Continued)

*Primary Examiner* — J. Christopher Ball
(74) *Attorney, Agent, or Firm* — Dinsmore & Shohl LLP

(57) ABSTRACT

A wireless near-field gas sensor system includes a wireless communications tag and a printed gas sensor. The wireless communications tag includes an integrated circuit and a wireless antenna. The printed gas sensor includes a sensor housing having one or more gas access regions, an electrolyte cavity positioned within the sensor housing, an electrolyte housed within the electrolyte cavity, and one or more electrodes positioned within the electrolyte cavity in electrochemical engagement with the electrolyte, and a resistor communicatively coupled to the one or more electrodes and the wireless communications tag.

55 Claims, 2 Drawing Sheets

(56) References Cited

U.S. PATENT DOCUMENTS

| | | |
|---|---|---|
| 5,438,876 A | 8/1995 | Lewis |
| 5,595,646 A | 1/1997 | Foos et al. |
| 5,670,949 A | 9/1997 | Kirby et al. |
| 5,876,577 A | 3/1999 | McAleer et al. |
| 5,945,069 A | 8/1999 | Buehler |
| 6,099,708 A | 8/2000 | Mallory et al. |
| 6,158,431 A | 12/2000 | Poole |
| 6,234,006 B1 | 5/2001 | Sunshine et al. |
| 6,254,794 B1 | 7/2001 | Yokota et al. |
| 6,454,923 B1 | 9/2002 | Dodgson et al. |
| 6,513,362 B1 | 2/2003 | Yadav et al. |
| 6,590,207 B2 | 7/2003 | Berger et al. |
| 6,645,361 B1 | 11/2003 | Bloemer et al. |
| 6,713,389 B2 | 3/2004 | Speakman |
| 6,936,147 B2 | 8/2005 | Prohaska et al. |
| 6,940,287 B2 | 9/2005 | Weyl et al. |
| 7,077,938 B1 | 7/2006 | Austen et al. |
| 7,189,341 B2 | 3/2007 | Li et al. |
| 7,279,080 B2 | 10/2007 | Chapples et al. |
| 7,422,646 B2 | 9/2008 | Prohaska et al. |
| 7,445,941 B2 | 11/2008 | Buechler |
| 8,152,991 B2 | 4/2012 | Briman et al. |
| 8,747,635 B2 | 6/2014 | Murakami et al. |
| 2002/0166769 A1 | 11/2002 | Serikov |
| 2003/0208133 A1 | 11/2003 | Mault |
| 2004/0135864 A1 | 7/2004 | Steinthal et al. |
| 2004/0213702 A1 | 10/2004 | Ingrisch |
| 2005/0274615 A1 | 12/2005 | Naito et al. |
| 2006/0096871 A1 | 5/2006 | Manoukian et al. |
| 2006/0191318 A1 | 8/2006 | McBride et al. |
| 2007/0102294 A1 | 5/2007 | Dorisio Deininger et al. |
| 2007/0144812 A1 | 6/2007 | Stewart et al. |
| 2007/0154748 A1 | 7/2007 | Okuyama et al. |
| 2008/0190174 A1 | 8/2008 | Kooi et al. |
| 2008/0202930 A1 | 8/2008 | Mett |
| 2008/0289962 A1 | 11/2008 | Prohaska et al. |
| 2009/0040044 A1 | 2/2009 | Chiao |
| 2009/0162750 A1 | 6/2009 | Kawakami et al. |
| 2010/0057401 A1 | 3/2010 | Scheffler et al. |
| 2010/0226824 A1 | 9/2010 | Ophir et al. |
| 2011/0226041 A1 | 9/2011 | Cummins |
| 2011/0246090 A1 | 10/2011 | Goya |
| 2011/0288430 A1 | 11/2011 | Varney et al. |
| 2012/0006096 A1 | 1/2012 | Ackley et al. |
| 2012/0125772 A1 | 5/2012 | Stetter et al. |
| 2012/0140431 A1 | 6/2012 | Faxvog et al. |
| 2013/0265140 A1 | 10/2013 | Gudan et al. |
| 2014/0018691 A1 | 1/2014 | McNeill |
| 2014/0029085 A1 | 1/2014 | Bond et al. |
| 2014/0174154 A1 | 6/2014 | Marra et al. |
| 2014/0208829 A1 | 7/2014 | Lechner et al. |
| 2014/0257127 A1 | 9/2014 | Smith et al. |
| 2014/0311905 A1 | 10/2014 | Stetter et al. |
| 2015/0338385 A1 | 11/2015 | Lee et al. |

FOREIGN PATENT DOCUMENTS

| | | |
|---|---|---|
| DE | 3809107 | 9/1989 |
| DE | 19832395 | 11/1999 |
| GB | 2440556 | 2/2008 |
| JP | 05-099886 | 4/1993 |
| JP | 08-327591 | 12/1996 |
| WO | 1990012315 | 10/1990 |
| WO | WO96/14576 | 5/1996 |
| WO | WO98/25138 | 6/1998 |
| WO | WO01/14864 | 3/2001 |
| WO | 20050114162 | 12/2005 |
| WO | 2013123500 | 8/2013 |
| WO | 2014143049 | 9/2014 |

OTHER PUBLICATIONS

V. Lakafosis, et al. "Progress Towards the First Wireless Sensor Networks Consisting of Inkjet-Printed Paper-Based RFID-Enabled Sensor Tags" Proceedings of the IEEE, vol. 98, No. 9, p. 1601-1609. (Year: 2010).*

International Search Report and Written Opinion issued in corresponding PCT Appln. No. PCT/US2016/034314, dated Sep. 2, 2016.

Wang, J., "Decentralized Electrochemical Monitoring of Trace Metals: From Disposable Strips to Remote Electrodes," Analyst 119:763-766 (1994).

Stetter, J.R., "Instrumentation to Monitor Chemical Exposure in the Synfuel Industry," Annals American Conf. of Governmental and Industrial Hygienists, 11:225-269 (1984).

Korotcenkov et al, "Review of Electrochemical Hydrogen Sensors," Chemical Reviews 109(3):1402-1433 (2009).

Stetter, J.R. et al, "Amperometric Gas Sensors—A Review," Modern Topics in Chemical Sensing: Chapter 4, Chemical Reviews, 108 (2):352-366 (2008).

Chang, S.C. et al, "Amperometric Gas Sensors", Talanta, 40(4):461-467 (1993).

International Search Report and Written Opinion issued in corresponding PCT International Application No. PCT/US2011/059075, dated Jan. 24, 2012.

International Search Report and Written Opinion issued in corresponding PCT International Application No. PCT/US2015/037893, dated Oct. 2, 2015.

International Search Report and Written Opinion issued in corresponding PCT International Application No. PCT/US2015/049631, dated Dec. 14, 2015.

International Search Report and Written Opinion issued in corresponding PCT International Application No. PCT/US2015/068251, dated Mar. 11, 2016.

International Search Report and Written Opinion issued in corresponding PCT International Application No. PCT/US2016/034314, dated Sep. 2, 2016.

International Search Report and Written Opinion issued in corresponding PCT International Application No. PCT/US2015/046053, dated Oct. 28, 2015.

* cited by examiner

WIRELESS NEAR-FIELD GAS SENSOR SYSTEM AND METHODS OF MANUFACTURING THE SAME

CROSS-REFERENCE TO RELATED APPLICATIONS

This application claims the benefit of U.S. Provisional Application Ser. No. 62/166,468, filed May 26, 2015.

TECHNICAL FIELD

The present specification generally relates to gas sensors, for example, printed gas sensors positioned in a wireless near-field gas sensor system.

BACKGROUND

Sensors including electrochemical cells are used for detection of certain gases, for example, toxic gases. Accordingly, there is a desire for wireless near-field gas sensor systems that include gas sensors and wireless near-field communication devices.

SUMMARY

In one embodiment, a wireless near-field gas sensor system includes a wireless communications tag and a printed gas sensor. The wireless communications tag includes a wireless communications integrated circuit and a wireless antenna. The printed gas sensor includes a sensor housing having one or more gas access regions, an electrolyte cavity positioned within the sensor housing, an electrolyte housed within the electrolyte cavity, one or more electrodes positioned within the electrolyte cavity in electrochemical engagement with the electrolyte, and a resistor communicatively coupled to the one or more electrodes and the wireless communications tag.

In another embodiment, a method of manufacturing a wireless near-field gas sensor system includes printing a printed wireless communications tag having a wireless communications integrated circuit and a printed wireless antenna and forming a printed gas sensor. Forming the printed gas sensor includes printing a sensor housing having one or more gas access regions and an electrolyte cavity positioned within the sensor housing, printing one or more electrodes and positioning the one or more electrodes within the electrolyte cavity, disposing an electrolyte within the electrolyte cavity such that the one or more electrodes positioned within the electrolyte cavity are in electrochemical engagement with the electrolyte, and positioning a resistor in electrical engagement with the one or more electrodes and the printed wireless communications tag.

In yet another embodiment, a wireless near-field gas sensor system includes a printed wireless communications tag, a printed gas sensor, a signal amplifier, and a wireless reader. The printed wireless communications tag includes a wireless communications integrated circuit, a wireless antenna, and a power harvesting circuit. The printed gas sensor includes a sensor housing having one or more gas access regions, an electrolyte cavity positioned within the sensor housing, an electrolyte housed within the electrolyte cavity, a working electrode positioned within the electrolyte cavity in electrochemical engagement with the electrolyte, a counter electrode, and a resistor communicatively coupled to the working electrode and the counter electrode. The signal amplifier is communicatively coupled to both the resistor of the printed gas sensor and the printed wireless communications tag. The wireless reader is configured to output an interrogation signal to interrogate the printed wireless communications tag. Further, the power harvesting circuit of the printed wireless communications tag is structurally configured to harvest energy from an electromagnetic field produced by the wireless reader when the wireless reader interrogates the printed wireless communications tag.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
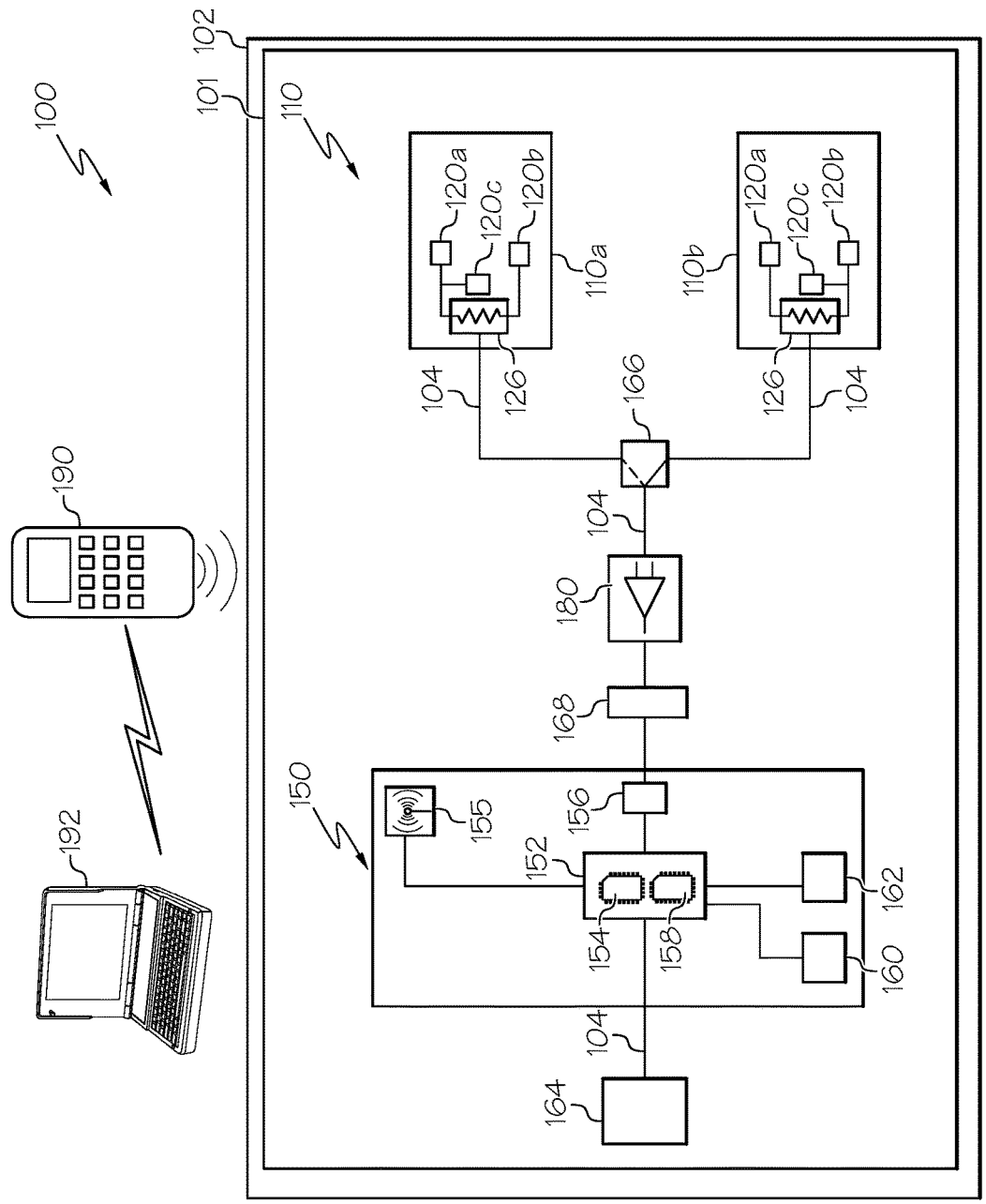
FIG. 1 schematically depicts a wireless near-field gas sensor system having a gas sensor and a wireless communications tag, according to one or more embodiments shown and described herein.

Embodiments described herein generally relate to wireless near-field gas sensor systems that include a printed gas sensor for detecting the presence and/or concentration of one or more target gases and a wireless communications tag communicatively coupled to the printed gas sensor for sending sensor data using near-field communications protocols. Referring now to FIG. 1, a wireless near-field gas sensor system 100 is schematically depicted. The wireless near-field gas sensor system 100 includes a wireless communications tag 150, a gas sensor 110 (e.g., a first gas sensor 110a and a second gas sensor 110b), and a signal amplifier 180. The gas sensor 110 is communicatively coupled to both the wireless communications tag 150 and the signal amplifier 180 such that a gas sensor signal output by the gas sensor 110, for example, when the gas sensor 110 detects a presence and/or concentration of a target gas, may be received by the wireless communications tag 150 and sent to a wireless reader 190 when the wireless reader 190 interrogates the wireless communications tag 150. Further, the signal amplifier 180 may be positioned between the gas sensor 110 and the wireless communications tag 150 such that the gas sensor signal output by the gas sensor 110 may be amplified by the signal amplifier 180.

Further, the gas sensor 110 is communicatively coupled to both the wireless communications tag 150 and the signal amplifier 180 using a communication path 104. The communication path 104 may be formed from any medium that is capable of transmitting a signal such as, for example, conductive wires, conductive traces, optical waveguides, or the like. In some embodiments, the communication path 104 may facilitate the transmission of wireless signals, such as wireless fidelity (Wi-Fi), Bluetooth, Bluetooth low energy, and the like. Moreover, the communication path 104 may be formed from a combination of mediums capable of transmitting signals.

In some embodiments, the wireless near-field gas sensor system 100 may comprise a common substrate 101 that provides a mounting location for the wireless communications tag 150, the gas sensor 110, and the signal amplifier 180. For example, the wireless communications tag 150, the gas sensor 110, and the signal amplifier 180 may each be coupled to the common substrate 101, for example, printed onto the common substrate 101. The common substrate 101 may comprise a flexible substrate material or a rigid substrate material. For example, the common substrate 101 may comprise a printed circuit board. Alternatively, the components of the wireless near-field gas sensor system 100 may be coupled to multiple substrates, for example, multiple printed circuit boards, or the like. Moreover, the wireless communications tag 150, the gas sensor 110, the signal amplifier 180 may each be housed together, for example, each be coupled to the common substrate 101 and housed together in a package housing 102.

The package housing 102 may hermetically seal some or all of the wireless near-field gas sensor system 100 within the package housing 102, for example, at least the wireless communications tag 150, the gas sensor 110, and the signal amplifier 180. Further, in embodiments in which the gas sensor 110 is positioned within the package housing 102, the package housing 102 may allow at least some gas access, such that the target gas may reach the gas sensor 110, for example, one or more gas access regions 122 of the gas sensor 110. In some embodiments, the package housing 102 may comprise polycarbonate, for example, a vacuum molded polycarbonate. In some embodiments, the package housing 102 and/or the common substrate 101 may be coupled to or integrated into a mobile computing device case, e.g., a mobile phone case. Further, the package housing 102 may comprise a thin aspect wearable or an internet-of-things device and may have thickness of between about 0.5 mm and about 2 mm, for example, 0.75 mm, 1 mm, 1.5 mm, or the like.

Figure 2:
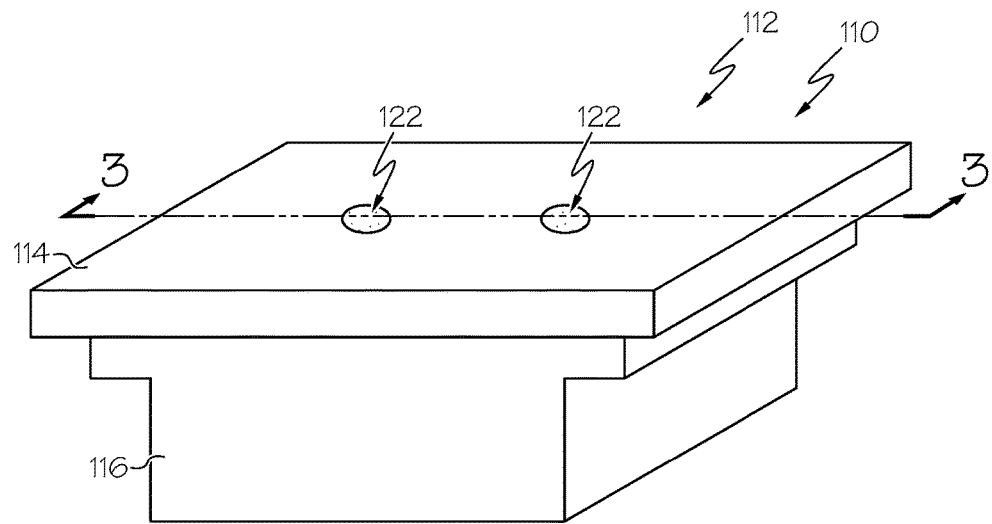
FIG. 2 schematically depicts an example gas sensor of the wireless near-field gas sensor system of FIG. 1, according to one or more embodiments shown and described herein.
Figure 3:
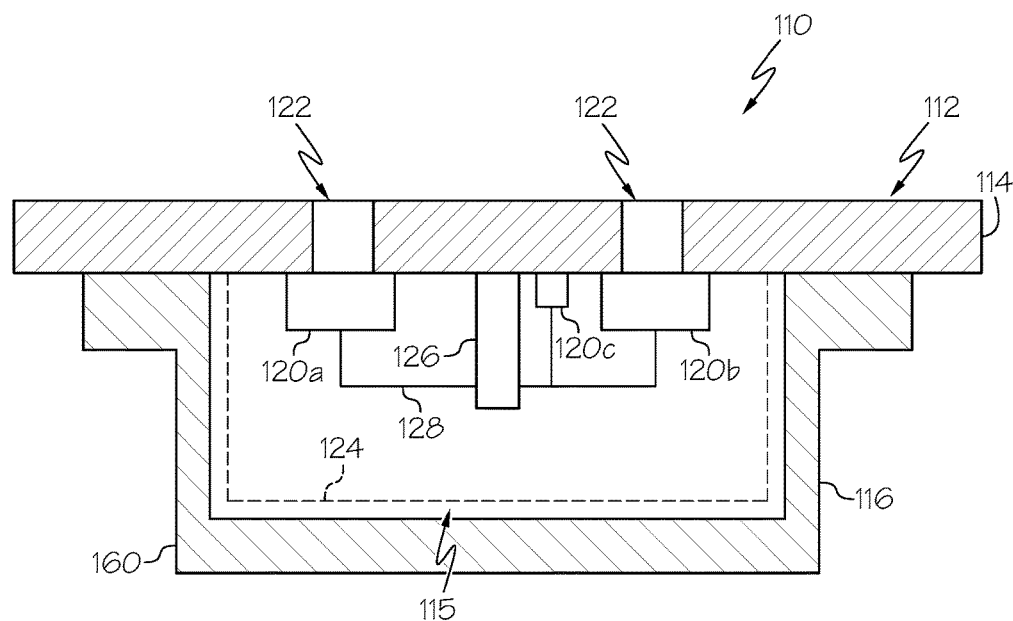
FIG. 3 schematically depicts a cross section of the gas sensor of FIG. 2, according to one or more embodiments shown or described herein.

Referring now to FIGS. 2 and 3, an example gas sensor 110 is schematically depicted. FIG. 2 depicts a perspective view of the gas sensor 110 and FIG. 3 depicts a cross-section view of the gas sensor 110 along line A-A of FIG. 2. The gas sensor 110 may comprise a printed gas sensor, for example the printed gas sensors disclosed in U.S. patent application Ser. No. 14/317,222 titled "Printed Gas Sensor," which is incorporated herein by reference, the printed gas sensors disclosed in U.S. Provisional Patent Application No. 62/028,543 titled "Printed Gas Sensor," hereby incorporated by reference. Further, in some embodiments, the gas sensor 110 may be the sensors disclosed in U.S. patent application Ser. No. 13/868,583 titled "Apparatus and Method for Microfabricated Multi-Dimensional Sensors and Sensing Systems," hereby incorporated by reference. In operation, the gas sensor 110 may measure a presence of the target gas in the gas sample and, in some embodiments, the gas sensor 110 may measure an amount and/or concentration of target gas in the gas sample. As an example and not a limitation, the target gas may comprise alcohol, ethanol and/or other hydrocarbons, Ketone, CO, OH—, $CH_3$, $CH_4$, $CO_2$, $O_3$, $H_2$, NO, $NO_2$, $SO_2$, $CH_4$, $O_2$, $H_2S$, other electrochemical compounds, and combinations thereof. Further, the one or more gas sensors 110 may comprise a MEMs sensor, an $SHO_2$ sensor for hydrocarbons, combustibles, or the like.

As depicted in FIGS. 2 and 3, the gas sensor 110 comprises a sensor housing 112, one or more electrodes 120, and an electrolyte cavity 115 positioned within the sensor housing 112 that houses a liquid, gel, and/or solid electrolyte in electrolytic contact with the one or more electrodes 120. The electrolyte cavity 115 may be hermetically sealed within the gas sensor 110, for example, within the sensor housing 112. The electrolyte cavity 115 may house the electrolyte, for example $H_2SO_4$, other acids, bases, salt solutions, ionic liquids, or combinations thereof. Moreover, the electrolyte cavity 115 may comprise a volume of about 250 $mm^3$ or less, for example, 200 $mm^3$, 150 $mm^3$, 100 $mm^3$, 50 $mm^3$, or the like.

The sensor housing 112 may comprise a single integral housing or may comprise one or more components coupled together using pressure sensitive adhesive, welding, bonding, or the like. For example, the sensor housing 112 may comprise a sensor substrate 114 coupled to an encapsulation housing 116 such that the electrolyte cavity 115 is positioned between the sensor substrate 114 and the encapsulation housing 116. Example material of the sensor housing 112 includes polycarbonate substrate, PET, PTFE, porous PTFE, tetrafluoroethylene (TFE) substrate, polyimide, glass, ceramic, or the like. Further, the sensor housing 112 comprises one or more gas access regions 122. In some embodiments, the gas access regions 122 may be fluidly coupled to the one or more electrodes 120 positioned within the electrolyte cavity 115 of the gas sensor 110 and may be configured to permit passage of the target gas into the electrolyte cavity 115.

Referring still to FIG. 3, the one or more electrodes 120 are positioned within the electrolyte cavity 115, for example, deposited in a pattern within the electrolyte cavity 115 onto a surface of the sensor substrate 114 and/or the encapsulation housing 116 that faces the electrolyte cavity 115. For example, the one or more electrodes 120 may be printed, for example, screen printed, inkjet printed, or the like, as well as stamped, or stenciled onto the sensor substrate 114 and/or the encapsulation housing 116. The one or more electrodes 120 may comprise a PTFE-metal composite electrode, for example, the electrodes described in the references incorporated by reference or any other know or yet to be developed electrode configured to perform electrochemistry. For example, the one or more electrodes 120 may comprise PTFE liquid, PTFE powder, polypropylene powder, and/or polyethylene powder, as well as catalysts, solvents, and additives, such as, for example, platinum, palladium, or alloys or supported catalysts like platinum on carbon. In some embodiments, the one or more electrodes 120 comprise asymmetrical electrodes. As a non-limiting example, the one or more electrodes 120 may comprise different sizes, different formulations (e.g. different % composites), and/or different materials (e.g. Pt and Pb, or Pt and C, or X and Y where X is responsive to the target gas and Y comprises a different material or geometry or composition than X).

In some embodiments, the one or more electrodes 120 may be coupled to one or more wicks 124 positioned within the electrolyte cavity 115. For example, the one or more electrodes 120 may be screen printed, inkjet printed, stamped, or stenciled onto the one or more wicks 124. The one or more wicks 124 may comprise a porous glass fiber, a glass fiber filter paper, a drop-on wick, or any other known or yet to be developed electrolyte matrix, and may facilitate electrolytic contact between the electrode 120 and the electrolyte. In some embodiments, the one or more wicks 124 may be may be coupled directly to the sensor housing 112.

Referring now to FIGS. 1 and 3, the one or more electrodes 120 are schematically depicted. As shown in FIGS. 1 and 3, the one or more electrodes 120 may comprise a first electrode 120a, a second electrode 120b, and a third electrode 120c. The first electrode 120a may comprise a working electrode configured to electrochemically react with the electrolyte and a target gas to generate an electrical signal at the first electrode 120a. Further, the second electrode 120b may comprise a counter electrode and the third electrode 120c may comprise a reference electrode. Further, in some embodiments, the one or more electrodes 120 may include multiple working electrodes, each configured to detect different target gases. For example, a first working electrode may be configured to detect CO and a second working electrode may be configured to detect gases such as $H_2S$, $O_3$, $SO_4$, or $NO_2$. In some embodiments, the electrical signal generated at the first electrode 120a may be linearly correlated with the concentration of a target gas present within the electrolyte cavity 115 due to the first order reaction rate at the working electrode. Moreover, the one or more electrodes 120 may comprise any number of working electrodes, references electrodes, and counter electrodes, and, in some embodiments, may comprise an equal number of working electrodes, reference electrodes, and counter electrodes.

As depicted in FIGS. 1 and 3, the gas sensor 110 may further comprise a resistor 126 communicatively coupled to the one or more electrodes 120. In some embodiments, the resistor 126 may be positioned within the gas sensor 110, for example, within the electrolyte cavity 115. In other embodiments, the resistor 126 may be positioned external to the gas sensor 110. Moreover, the resistor 126 may be positioned between the first electrode 120a (e.g., the working electrode) and the second electrode 120b (e.g., the counter electrode) such that an electrical signal (e.g., an electrical closed loop current) generated at the first electrode 120a from the electrochemical reaction between the first electrode 120a, the electrolyte, and the target gas is received by the resistor 126 (e.g., traverses the resistor 126). In some embodiments, the resistor 126 comprises a printed resistor.

In operation, upon receipt of the electrical signal, the resistor 126 is configured to generate a voltage correlated with the current of the electrical signal generated at the first electrode 120a and output the voltage into the communication path 104 such that the gas sensor signal may be received by the signal amplifier 180 and the wireless communications tag 150. In some embodiments, the resistor 126 may comprise a customizable resistor, for example, a range selectable resistor bank. The range selectable resistor bank provides selectable resistor values, which may be selected based on the desired response time, the gain of the gas sensor signal, and the desired signal-to-noise ratio.

The gas sensor 110 may further comprise one or more electrically conductive printed runners 128, such as conductive traces, positioned in electrical and/or electrochemical contact with the one or more electrodes 120 and the resistor 126 to provide an electrical pathway for an electrical signal produced by an electrochemical reaction at the one or more electrodes 120. Further, the one or more electrically conductive printed runners 128 may be communicatively coupled to the communication path 104 to carry the gas sensor signal out of the gas sensor 110 to the communication path 104, for example, using one or more vias extending through the sensor housing 112. The electrically conductive printed runners 128 may comprise carbon or a vapor deposition of a metal such as, for example, Au, Pd, Pt, Jr, Ru, and the like.

In operation, in response to the presence of the target gas, the one or more electrodes 120 may generate a current to target gas concentration ratio of between about 0.1 nA/ppm and about 4 nA/ppm, for example, 0.3 nA/ppm, 0.5 nA/ppm, 1 nA/ppm, 1.5 nA/ppm, 2 nA/ppm, 2.5 nA/ppm, 3 nA/ppm, 3.5 nA/ppm, or the like. Further, in one example embodiment, when the one or more electrodes 120 generate a current of about 2 nA/ppm, a 10 K Ohm resistor 126 outputs a gas sensor signal comprising a voltage to target gas concentration ratio of about 20 microvolts/ppm and a 150 K Ohm resistor 126 outputs a gas sensor signal comprising a voltage to target gas concentration ratio of about a 0.3 millivolts/ppm. Further, the power of the gas sensor signal output by the gas sensor 110 may comprise about 100 μW or less, for example, 90 μW, 75 μW, 50 μW, 25 μW, or the like. Moreover, the gas sensor 110 is scalable to produce stronger or weaker gas sensor signals. For example, a larger gas sensor 110 may output a larger gas sensor signal and a smaller gas sensor 110 may output a smaller gas sensor signal. In some embodiments, it may be desirable to have smaller gas sensor 110 and thus, it may be desirable to amplify the gas sensor signal, for example, using the signal amplifier 180. Moreover, the gas sensor 110 may be configured to measure target gas concentrations of between about 0.1 ppm to about 1000 ppm, for example, between about 1 ppm and about 10 ppm.

Referring again to FIG. 1, the signal amplifier 180 is electrically coupled to both the wireless communications tag 150 and the gas sensor 110, for example, positioned between the gas sensor 110 and the wireless communications tag 150 such that the gas sensor signal output by the gas sensor 110 traverses the signal amplifier 180 before reaching the wireless communications tag 150. In particular, the signal amplifier 180 may be communicatively coupled to the resistor 126 of the gas sensor 110. The signal amplifier 180 may comprise an operational amplifier such as a low power operational amplifier, a variable gain operational amplifier circuit, or the like. In some embodiments, the operational amplifier comprises one or more printed transistors. Further, the signal amplifier 180 may comprise a differential amplifier, two transistor current mirror circuit, or any other known or yet to be developed signal amplifier. In operation, the signal amplifier 180 increases the voltage gain of the gas sensor signal output by the gas sensor 110. For example, the signal amplifier 180 may be configured to increase the gain by 10 times or more, for example, 10 times, 100 times, 1,000 times, 10,000 times, or the like. In some embodiments, for example, when the signal amplifier 180 comprises a variable gain operation amplifier circuit, the signal amplifier 180 may increase the signal to noise ratio of the gas sensor signal output by the gas sensor 110. Moreover, the signal amplifier 180 may comprise a printed signal amplifier, for example, printed onto the common substrate 101.

As depicted in FIG. 1, the wireless near-field gas sensor system 100 may further comprise an analog-to-digital converter 156. In some embodiments, the analog-to-digital converter 156 may be a component of the wireless communications tag 150. In other embodiments, the analog-to-digital converter 156 may be positioned external the wireless communications tag 150, for example, positioned between the gas sensor 110 and the wireless communications tag 150 such that the gas sensor signal output by the gas sensor 110 traverses the analog-to-digital converter 156 before reaching the wireless communications tag 150. In operation, the gas sensor signal output by the gas sensor 110 may comprise an analog signal and the analog-to-digital converter 156 may convert the analog signal into a digital signal. Further, in some embodiments, the analog-to-digital converter 156 may be used to amplify the gas sensor signal, for example, in embodiments that do not include the signal amplifier 180. For example, the analog-to-digital converter 156 may be configured to digitally represent a target gas measurement of about 1 ppm as about 1 byte to about 200 bytes, for example, about 10 bytes, 25 bytes, 50 bytes, 100 bytes, or the like.

In some embodiments, the wireless near-field gas sensor system 100 may further comprise a temperature sensor 164 communicatively coupled to the wireless communications tag 150 using the communication path 104. In operation, the temperature sensor 164 may measure the temperature and output a temperature signal to the wireless communications tag 150. Moreover, the temperature measured by the temperature sensor 164 may be associated with the gas sensor signal measured by the gas sensor 110 allowing the wireless near-field gas sensor system 100 to account for any alterations to the gas sensor signal caused by temperature. In some embodiments, the temperature sensor 164 may comprise a thermistor, for example, a printed thermistor. Further, the temperature sensor 164 may comprises a printed temperature sensor 164, for example, printed onto the common substrate 101. Moreover, while the temperature sensor 164 is depicted external to the wireless communications tag 150, in some embodiments, the temperature sensor 164 may be positioned within the wireless communications tag 150.

As depicted in FIG. 1, the wireless near-field gas sensor system 100 may comprise one or more signal filters 168 positioned between the gas sensor 110 and the wireless communications tag 150 such that the gas sensor signal output by the one or more gas sensors 110 is filtered by the one or more signal filters 168 before reaching the wireless communications tag 150, increasing the signal to noise ratio of the gas sensor signal. In some embodiments, the one or more signal filters 168 comprise a voltage filter, such as a voltage follower, a low pass filter, a high pass filter, or the like. Further, the one or more signal filters 168 may comprises a printed signal filters 168, for example, printed onto the common substrate 101. Moreover, while the one or more signal filters 168 are depicted external to the wireless communications tag 150 in FIG. 1, the one or more signal filters 168 may be components of the wireless communications tag 150.

Referring again to FIG. 1, the wireless communications tag 150 comprises at least a wireless communications integrated circuit 152 and a wireless antenna 155. The wireless communications tag 150 may further comprise a processor 154 and a recording memory module 158, which may each be positioned in the wireless communications integrated circuit 152. Further, the one or more recording memory modules 158 may comprise RAM, ROM, flash memories, hard drives, cloud based memory, or the like. In operation, the recording memory module 158 is configured to record and store gas sensor data regarding the presence of a target gas (e.g., the gas sensor signal), temperature data (e.g., the temperature signal), and the time of measurement by the gas sensor 110 and/or the temperature sensor 164. In some embodiments, at least a portion of the wireless communications tag 150 is printed, for example, the wireless antenna 155 may comprise a printed wireless antenna 155, for example, printed onto the common substrate 101. Further, the wireless communications tag 150 may comprise a printed tag, for example, printed onto the common substrate 101. In some embodiments, the wireless communications tag 150 may comprise one or more passive printed components, for example, components powered by energy received from the interrogation signal of the wireless reader 190 that are powered on only upon receipt of the interrogation signal, one or more active printed components, for example, components that are constantly powered on, such as components coupled to the power supply 162, or a combination of passive printed components and active printed components. Moreover, in some embodiments, the wireless communications tag 110 and the gas sensor 110 are coupled together, for example, integrated into a unitary structure.

The wireless communications tag 150, for example, the wireless communications integrated circuit 152 of the wireless communications tag 150, may comprise near-field communication hardware configured to operate near-field communication protocols, for example, radio-frequency identification (RFID), near-field communication (NFC), such as high frequency NFC, or the like. For example, the wireless communications tag 150 may send and receive RFID signals, NFC signals, or the like, using the wireless antenna 155. In some embodiments, the wireless communications tag 150 may comprise a passive ISO 15693 tag chip.

Referring still to FIG. 1, the wireless near-field gas sensor system 100 further comprises a wireless reader 190. The wireless reader 190 is configured to output an interrogation signal to interrogate the wireless communications tag 150, and in response, receive sensor signal data and/or temperature signal data from the wireless communications tag 150. In some embodiments, the wireless reader 190 is a computing device, for example, a mobile computing device such as a smart phone, tablet, or the like. In some embodiments, the wireless reader 190 may be communicatively coupled to an external computing device 192. In operation, the wireless reader 190 and/or the external computing device 192 may receive the sensor signal data and/or temperature signal data for display, storage, analysis, manipulation, or the like. For example, the sensor signal data and/or temperature signal data may be accessible and viewable using the wireless reader 190 and/or the external computing device 192, such that the environmental history of the area where the gas sensor 110 is located may be accessed and viewed. Further, the wireless reader 190, the wireless communications tag 150, and/or the external computing device 192, may provide temperature compensation to account for the temperature measured by the temperature sensor 164, for example, using any known or yet to be developed temperature correction and compensation algorithms.

In operation, the wireless reader 190 and/or the external computing device 192 may display or otherwise report environmental conditions, such as target gas presence, target gas concentration, temperature, either on demand (e.g., in response to user input) or at regular intervals. Further, the wireless reader 190 and/or the external computing device 192 may provide alerts regarding target gas presence, target gas concentration, temperature, and other conditions. The alerts may be audible, visual, or tactile. In some embodiments, the wireless reader 190 and/or the external computing device 192 may be positioned in a base station, for example a wireless compact powered base station. In one example embodiment, the wireless reader 190 and/or the external computing device 192 may be configured to analyze and record sensor signal data and/or temperature data for an exposure period, for example, between about 2 and about 12 hours, such as 4 hours, 6 hours, 8 hours, 10 hours, or the like. The measurements over the exposure period may be compared with historical measurement levels, for example, the sensor signal data measured by the gas sensor 110 over the lifetime of the gas sensor 110.

Referring again to FIG. 1, the wireless near-field gas sensor system 100 may further comprise a power harvesting circuit 160. The power harvesting circuit 160 is structurally configured to harvest energy from an electromagnetic field produced by a wireless reader 190 when the wireless reader 190 interrogates the wireless communications tag 150. The power harvesting circuit 160 allows at least some of the components of the wireless near-field gas sensor system 100 to operate without a constant power supply. In operation, the energy harvested by the power harvesting circuit 160 may be used to power other components of the wireless near-field gas sensor system 100, for example, the wireless communications tag 150, the analog-to-digital converter 156, the temperature sensor 164, the signal amplifier 180, or the like. Moreover, the wireless near-field gas sensor system 100, for example, the wireless communications tag 150, may further comprise a power supply 162, for example, a battery such as a printed battery, a charging component, or the like. In some embodiments, the power harvesting circuit 160 is printed, for example, onto the common substrate 101. Further, in some embodiments, the power harvesting circuit 160 comprises one or more printed passive components, printed active components, or combinations thereof.

Referring still to FIG. 1, the wireless near-field gas sensor system 100 may further comprise an integrated component switch 166 communicatively coupled to the wireless communications tag 150 and the one or more gas sensors 110. The integrated component switch 166 may comprise any switching device, for example, a steady state switch, a mechanical switch, or the like, and may selectively engage the wireless communications tag 150 with an individual gas sensor 110. For example, as depicted in FIG. 1, the wireless near-field gas sensor system 100 may comprise a first gas sensor 110a and a second gas sensor 110b and the integrated component switch 166 is communicatively coupled to both the first gas sensor 110a and the second gas sensor 110b. Moreover, the integrated component switch 166 may be powered by energy harvested by the power harvesting circuit 160.

The integrated component switch 166 is structurally configured to selectively engage the first gas sensor 110a or the second gas sensor 110b with the wireless communications tag 150. For example, the integrated component switch 166 may comprise a series RC branch, which, in operation, provides a varying voltage to one or more inverting gates. The inverting gates can then provide a voltage to the enabling pins of multiple gain amplifiers, each of which is connected to a different gas sensor 110. The integrated component switch 166 may be powered by the power harvesting circuit 160. Moreover, in embodiments comprising two or more gas sensors 110, an individual analog-to-digital converter 156 may be communicatively coupled to each individual gas sensor 110, for example, positioned between the integrated component switch 166 and each individual gas sensor 110.

In operation, the wireless near-field gas sensor system 100 may be used for carbon monoxide monitoring, health protection, fire detection, security, wellness, environmental and similar applications. For example, the wireless near-field gas sensor system 100 may be able to monitor and report potential environmental hazards caused by any measurable target gas. Moreover, the wireless communications tag 150 of the wireless near-field gas sensor system 100 may be interrogated by the wireless reader 190 through windows, doors, walls, or other structures.

Referring again to FIGS. 1-3, a method of manufacturing the wireless near-field gas sensor system 100 will now be described. While the steps of the method are described below in a particular order, it should be understood that other orders are contemplated. The method includes printing the wireless communications tag 150 having at least a wireless communications integrated circuit 152 and a printed wireless antenna 155. For example, the printed wireless communications tag 150 may be printed onto a substrate such as the common substrate 101. In some embodiments, printing the wireless communications tag 150 further comprises printing the power harvesting circuit 160, for example, onto the common substrate 101.

The method further comprises forming the gas sensor 110, for example, a printed gas sensor. Forming the gas sensor 110 includes forming a sensor housing 112 having one or more gas access regions 122 and an electrolyte cavity 115 positioned within the sensor housing 112. In some embodiments, the sensor housing 112 may be formed by printing the sensor housing 112. In other embodiments, the sensor housing 112 may be formed by coupling the sensor substrate 114 to the encapsulation housing 1156, for example, bonding, adhering, or the like. Forming the gas sensor 110 further comprises printing the one or more electrodes 120 and positioning the one or more electrodes 120 within the electrolyte cavity 115. Next, the electrolyte may be disposed within the electrolyte cavity 115 such that the one or more electrodes 120 positioned within the electrolyte cavity 115 are in electrochemical engagement with the electrolyte. Further, the resistor 126 may be positioned in electrical engagement with the one or more electrodes 120. In some embodiments, the gas sensor 110 may be printed onto the common substrate 101. Next, the signal amplifier 180 may be positioned in electrical engagement with both the resistor 126 of the gas sensor 110 and the wireless communications tag 150. The signal amplifier 180 may be printed, for example, on the common substrate 101. In particular, the signal amplifier 180 may be printed before the signal amplifier 180 is positioned in electrical engagement with both the printed gas sensor 110 and the wireless communications tag 150. Moreover, in some embodiments, the wireless communications tag 150, the printed gas sensor 110, and the signal amplifier 180 may be positioned and sealed within the package housing 102.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A wireless near-field gas sensor system comprising a wireless communications tag and a printed gas sensor, wherein:
   the wireless communications tag comprises a wireless communications integrated circuit and a wireless antenna; and
   the printed gas sensor comprises:
      a sensor housing having one or more gas access regions;
      an electrolyte cavity positioned within the sensor housing;
      an electrolyte housed within the electrolyte cavity;
      one or more electrodes positioned within the electrolyte cavity in electrochemical engagement with the electrolyte; and
      a printed resistor communicatively coupled the one or more electrodes and the wireless communications tag.

2. The wireless near-field gas sensor system of claim 1, wherein the sensor housing comprises a sensor substrate coupled to an encapsulation housing such that the electrolyte cavity is positioned between the sensor substrate and the encapsulation housing.

3. The wireless near-field gas sensor system of claim 1, wherein the one or more electrodes comprise printed electrodes.

4. The wireless near-field gas sensor system of claim 1, wherein:
the one or more electrodes comprise a first electrode and a second electrode; and
the first electrode comprises a working electrode configured to electrochemically react with the electrolyte and a target gas to generate an electrical signal at the first electrode.

5. The wireless near-field gas sensor system of claim 4, wherein the printed resistor is positioned between the first electrode and the second electrode such that the electrical signal generated by the first electrode traverses the printed resistor.

6. The wireless near-field gas sensor system of claim 4, wherein the electrical signal generated at the first electrode is linearly correlated with a concentration of a target gas present within the electrolyte cavity.

7. The wireless near-field gas sensor system of claim 4, wherein:
the second electrode comprises a counter electrode;
the one or more electrodes further comprise a third electrode; and
the third electrode comprises a reference electrode.

8. The wireless near-field gas sensor system of claim 1, wherein the printed resistor comprises a range selectable resistor bank.

9. The wireless near-field gas sensor system of claim 1, wherein:
the printed gas sensor further comprises one or more electrically conductive printed runners electrically coupled to the one or more electrodes and the printed resistor to provide an electrical pathway for an electrical signal produced by an electrochemical reaction at the one or more electrodes; and
the one or more electrodes comprise printed electrodes.

10. The wireless near-field gas sensor system of claim 9, further comprising a signal amplifier communicatively coupled to both the printed resistor of the printed gas sensor and the wireless communications tag.

11. The wireless near-field gas sensor system of claim 10, wherein the signal amplifier comprises an operational amplifier.

12. The wireless near-field gas sensor system of claim 11, wherein the operational amplifier is a variable gain operational amplifier.

13. The wireless near-field gas sensor system of claim 11, wherein the operational amplifier comprises one or more printed transistors.

14. The wireless near-field gas sensor system of claim 10, wherein the signal amplifier comprises a differential amplifier or a two transistor current minor circuit.

15. The wireless near-field gas sensor system of claim 10, wherein the signal amplifier is a printed signal amplifier.

16. The wireless near-field gas sensor system of claim 1, wherein the wireless communications integrated circuit of the wireless communications tag comprises a processor and an analog-to-digital converter.

17. The wireless near-field gas sensor system of claim 1, wherein the wireless antenna of the wireless communications tag comprises a printed wireless antenna.

18. The wireless near-field gas sensor system of claim 1, wherein the wireless communications tag comprises a printed wireless communications tag.

19. The wireless near-field gas sensor system of claim 18, wherein the printed wireless communications tag comprises one or more passive printed components.

20. The wireless near-field gas sensor system of claim 18, wherein the printed wireless communications tag comprises one or more active printed components.

21. The wireless near-field gas sensor system of claim 1, wherein the wireless communications tag is configured to operate a radio-frequency identification protocol.

22. The wireless near-field gas sensor system of claim 1, wherein the wireless communications tag is configured to operate a near-field communication protocol.

23. The wireless near-field gas sensor system of claim 1, wherein the wireless communications tag is integrated with the printed gas sensor.

24. The wireless near-field gas sensor system of claim 1, further comprises a power harvesting circuit configured to harvest energy from an electromagnetic field produced by a wireless reader when the wireless reader interrogates the wireless communications tag.

25. The wireless near-field gas sensor system of claim 24, wherein the power harvesting circuit comprises one or more printed passive components.

26. The wireless near-field gas sensor system of claim 24, wherein the power harvesting circuit comprises one or more printed active components.

27. The wireless near-field gas sensor system of claim 1, further comprising a wireless reader configured to output an interrogation signal to interrogate the wireless communications tag and, upon interrogation of the wireless communications tag, receive gas sensor data, temperature data, or both from the wireless communications tag.

28. The wireless near-field gas sensor system of claim 1, further comprising a recording memory module communicatively coupled to the printed gas sensor, wherein the recording memory module is configured to record and store gas sensor data regarding a presence of a target gas.

29. The wireless near-field gas sensor system of claim 1, further comprising an analog-to-digital converter communicatively coupled to the wireless communications tag and the printed gas sensor.

30. The wireless near-field gas sensor system of claim 29, wherein the analog-to-digital converter is configured to convert an analog gas sensor signal output by the printed gas sensor into a digital gas sensor signal and amplify the digital gas sensor signal.

31. The wireless near-field gas sensor system of claim 29, wherein the analog-to-digital converter is positioned between the printed gas sensor and the wireless communications tag such that a gas sensor signal output by the printed gas sensor traverses the analog-to-digital converter before reaching the wireless communications tag.

32. The wireless near-field gas sensor system of claim 1, further comprising a temperature sensor communicatively coupled to the wireless communications tag.

33. The wireless near-field gas sensor system of claim 32, wherein the temperature sensor comprises a printed thermistor.

34. The wireless near-field gas sensor system of claim 1, further comprising an integrated component switch communicatively coupled to the wireless communications tag.

35. The wireless near-field gas sensor system of claim 34, wherein:

the printed gas sensor comprises a first printed gas sensor and the wireless near-field gas sensor system further comprises a second printed gas sensor;

the integrated component switch is communicatively coupled to the first printed gas sensor, the second printed gas sensor, and the wireless communications tag; and the integrated component switch is structurally configured to selectively engage the wireless communications tag with the first printed gas sensor or the second printed gas sensor.

36. The wireless near-field gas sensor system of claim 1, further comprising one or more signal filters communicatively coupled to the printed gas sensor and the wireless communications tag.

37. The wireless near-field gas sensor system of claim 36, wherein the one or more signal filters comprise a voltage filter, a low pass filter, a high pass filter, or combinations thereof.

38. The wireless near-field gas sensor system of claim 1, further comprising a common substrate, wherein the wireless communications tag, the printed gas sensor, and a signal amplifier are each coupled to the common substrate, and wherein the common substrate comprises a flexible substrate material.

39. The wireless near-field gas sensor system of claim 38, wherein the wireless communications tag, the printed gas sensor, and the signal amplifier are each printed onto the common substrate.

40. The wireless near-field gas sensor system of claim 1, wherein the printed resistor is housed within the electrolyte cavity of the printed gas sensor.

41. A method of manufacturing a wireless near-field gas sensor system, the method comprising:

printing a printed wireless communications tag comprising a wireless communications integrated circuit and a printed wireless antenna; and forming a printed gas sensor, wherein forming the printed gas sensor comprises:

forming a sensor housing having one or more gas access regions and an electrolyte cavity positioned within the sensor housing;

printing one or more electrodes and positioning the one or more electrodes within the electrolyte cavity;

disposing an electrolyte within the electrolyte cavity such that the one or more electrodes positioned within the electrolyte cavity are in electrochemical engagement with the electrolyte; and printing a resistor and positioning the resistor in electrical engagement with the one or more electrodes and a wireless communications tag, wherein the wireless communications tag comprises a wireless communications integrated circuit and a wireless antenna.

42. The method of claim 41, further comprising positioning a signal amplifier in electrical engagement with both the resistor of the printed gas sensor and the wireless communications tag.

43. The method of claim 42, further comprising printing the signal amplifier.

44. The method of claim 43, wherein the signal amplifier is printed before the signal amplifier is positioned in electrical engagement with both the resistor of the printed gas sensor and the wireless communications tag.

45. The method of claim 41, wherein the wireless communications tag further comprises a power harvesting circuit.

46. The method of claim 41, wherein the wireless communications tag and the printed gas sensor are each disposed on a common substrate and the method further comprises printing a signal amplifier onto the common substrate such that the signal amplifier is in electrical engagement with both the resistor of the printed gas sensor and the wireless communications tag.

47. The method of claim 41, wherein the resistor is housed within the electrolyte cavity of the printed gas sensor.

48. A wireless near-field gas sensor system comprising a wireless communications tag, a printed gas sensor, a signal amplifier, and a wireless reader, wherein:

the wireless communications tag comprises a wireless communications integrated circuit, a wireless antenna, and a power harvesting circuit;

the printed gas sensor comprises:

a sensor housing having one or more gas access regions;

an electrolyte cavity positioned within the sensor housing;

an electrolyte housed within the electrolyte cavity;

a working electrode positioned within the electrolyte cavity in electrochemical engagement with the electrolyte;

a counter electrode; and a printed resistor communicatively coupled to the working electrode and the counter electrode;

the signal amplifier is communicatively coupled to both the printed resistor of the printed gas sensor and the wireless communications tag; and the wireless reader is configured to output an interrogation signal to interrogate the wireless communications tag, wherein the power harvesting circuit of the wireless communications tag is structurally configured to harvest energy from an electromagnetic field produced by the wireless reader when the wireless reader interrogates the wireless communications tag.

49. The wireless near-field gas sensor system of claim 48, wherein the wireless communications tag comprises a recording memory module communicatively coupled to the printed gas sensor, wherein the recording memory module is configured to record and store gas sensor data regarding a presence of a target gas.

50. The wireless near-field gas sensor system of claim 49, wherein the gas sensor data stored in the recording memory module is retrievable by the wireless reader when the wireless reader interrogates the wireless communications tag.

51. The wireless near-field gas sensor system of claim 48, wherein the printed resistor is housed within the electrolyte cavity of the printed gas sensor.

52. A wireless near-field gas sensor system comprising a wireless communications tag and a printed gas sensor, wherein:

the wireless communications tag comprises a wireless communications integrated circuit and a wireless antenna; and the printed gas sensor comprises:

a sensor housing having one or more gas access regions;

an electrolyte cavity positioned within the sensor housing;

an electrolyte housed within the electrolyte cavity;

one or more electrodes positioned within the electrolyte cavity in electrochemical engagement with the electrolyte; wherein:

the one or more electrodes comprise a first electrode and a second electrode;

the first electrode comprises a working electrode configured to electrochemically react with the electrolyte and a target gas to generate an electrical signal at the first electrode; and the second electrode comprises a counter electrode; and a resistor communicatively coupled to the one or more electrodes and the wireless communications tag, wherein the resistor is positioned between the working electrode and the counter electrode such that the electrical signal generated by the working electrode traverses the resistor.

53. A wireless near-field gas sensor system comprising a wireless communications tag and a printed gas sensor, wherein:

the wireless communications tag comprises a wireless communications integrated circuit and a wireless antenna; and the printed gas sensor comprises:

a sensor housing having one or more gas access regions;

an electrolyte cavity positioned within the sensor housing;

an electrolyte housed within the electrolyte cavity;

one or more electrodes positioned within the electrolyte cavity in electrochemical engagement with the electrolyte; and a resistor communicatively coupled to the one or more electrodes and the wireless communications tag, wherein the resistor comprises a range selectable resistor bank.

54. A wireless near-field gas sensor system comprising a wireless communications tag and a printed gas sensor, wherein:

the wireless communications tag comprises a wireless communications integrated circuit and a wireless antenna; and the printed gas sensor comprises:

a sensor housing having one or more gas access regions;

an electrolyte cavity positioned within the sensor housing;

an electrolyte housed within the electrolyte cavity;

one or more electrodes positioned within the electrolyte cavity in electrochemical engagement with the electrolyte, wherein the one or more electrodes comprise printed electrodes; and a resistor communicatively coupled to the one or more electrodes and the wireless communications tag; and a signal amplifier communicatively coupled to both the resistor of the printed gas sensor and the wireless communications tag.

55. The wireless near-field gas sensor system of claim 54, wherein the printed gas sensor further comprises one or more electrically conductive printed runners electrically coupled to the one or more electrodes and the resistor to provide an electrical pathway for an electrical signal produced by an electrochemical reaction at the one or more electrodes.

* * * * *